(12) United States Patent
Albertorio et al.

(10) Patent No.: US 10,070,891 B2
(45) Date of Patent: Sep. 11, 2018

(54) METHODS AND APPARATUS FOR INTERNAL HIP DISTRACTION

(71) Applicant: Arthrex, Inc., Naples, FL (US)

(72) Inventors: Ricardo Albertorio, Naples, FL (US); John P. Gauldoni, Naples, FL (US)

(73) Assignee: ARTHREX, INC., Naples, FL (US)

( * ) Notice: Subject to any disclaimer, the term of this patent is extended or adjusted under 35 U.S.C. 154(b) by 305 days.

(21) Appl. No.: 14/838,723

(22) Filed: Aug. 28, 2015

(65) Prior Publication Data

US 2017/0056072 A1    Mar. 2, 2017

(51) Int. Cl.
*A61F 5/00* (2006.01)
*A61B 17/66* (2006.01)
*A61B 17/04* (2006.01)
*A61B 17/64* (2006.01)

(52) U.S. Cl.
CPC .......... *A61B 17/66* (2013.01); *A61B 17/0401* (2013.01); *A61B 17/6408* (2013.01); *A61B 2017/0404* (2013.01); *A61B 2017/0445* (2013.01)

(58) Field of Classification Search
None
See application file for complete search history.

(56) References Cited

U.S. PATENT DOCUMENTS

| | | | |
|---|---|---|---|
| 6,755,865 B2 | 6/2004 | Tarabishy | |
| 8,672,947 B2 | 3/2014 | Flom | |
| 8,721,649 B2 | 5/2014 | Gifford | |
| 8,828,008 B2 | 9/2014 | Stubbs | |
| 8,858,563 B2 | 10/2014 | Philippon et al. | |
| 2007/0168036 A1 | 7/2007 | Ainsworth et al. | |
| 2009/0312807 A1 | 12/2009 | Boudreault et al. | |
| 2011/0152868 A1 | 6/2011 | Kourtis et al. | |
| 2011/0166579 A1 | 7/2011 | Deem et al. | |
| 2011/0282387 A1 | 11/2011 | Suh et al. | |
| 2012/0239046 A1 | 9/2012 | Kaiser et al. | |
| 2012/0240938 A1 | 9/2012 | Pamichev | |
| 2013/0131444 A1 | 5/2013 | Boudreault et al. | |
| 2013/0231671 A1 | 9/2013 | Boudreault et al. | |
| 2014/0277185 A1 | 9/2014 | Boileau et al. | |
| 2014/0378982 A1 | 12/2014 | Philippon et al. | |
| 2015/0057668 A1 | 2/2015 | Chehab et al. | |
| 2015/0196342 A1 | 7/2015 | Suddaby | |

FOREIGN PATENT DOCUMENTS

| | | |
|---|---|---|
| WO | 99/37219 | 7/1999 |
| WO | 2006/135935 A1 | 12/2006 |
| WO | WO 2012/064786 A1 | 5/2012 |
| WO | 2013/052807 A2 | 4/2013 |

OTHER PUBLICATIONS

International Search Report and Written Opinion of the International Searching Authority for International Application No. PCT/US2016/047234 dated Jan. 30, 2017.
Stryker "Dynamic Joint Distractor II, External Fixation System." 2006.
International Preliminary Report on Patentability for International Application No. PCT/US2016/047234 dated Mar. 15, 2018.

*Primary Examiner* — Sameh Boles
(74) *Attorney, Agent, or Firm* — Carlson, Gaskey & Olds

(57) ABSTRACT

This present invention relates to medical procedures and distraction devices for internal joint distraction.

6 Claims, 4 Drawing Sheets

METHODS AND APPARATUS FOR INTERNAL HIP DISTRACTION

BACKGROUND

This disclosure relates to surgical methods and devices for internal joint distraction. In particular, the devices and methods described herein utilize less force and cause less collateral damage than existing joint distraction systems.

SUMMARY

Disclosed herein are medical devices and methods for internally distracting joints by using minimally invasive distraction. Minimally invasive devices are deployed within a portion of a bone proximal to a bone joint, e.g., in the greater trochanter, and which allow direct force application to the joint to be distracted. The disclosed devices are used in medical procedures for treating/correcting/repairing damage/diseased articular joints, e.g., avascular necrosis of the hip, arthritis in younger people, femoral-cetabular impingements, etc.

In an illustrative embodiment, a method of distracting a bone joint is disclosed and includes forming a passage in one bone of a bone joint; arranging an anchor assembly in the passage; and applying a force directly to the anchor assembly to separate and distract the one bone from another bone of the bone joint. An exemplary method includes distracting the bone joint between the femoral head and the acetabulum or the glenohumeral joint.

DETAILED DESCRIPTION

Figure 1:
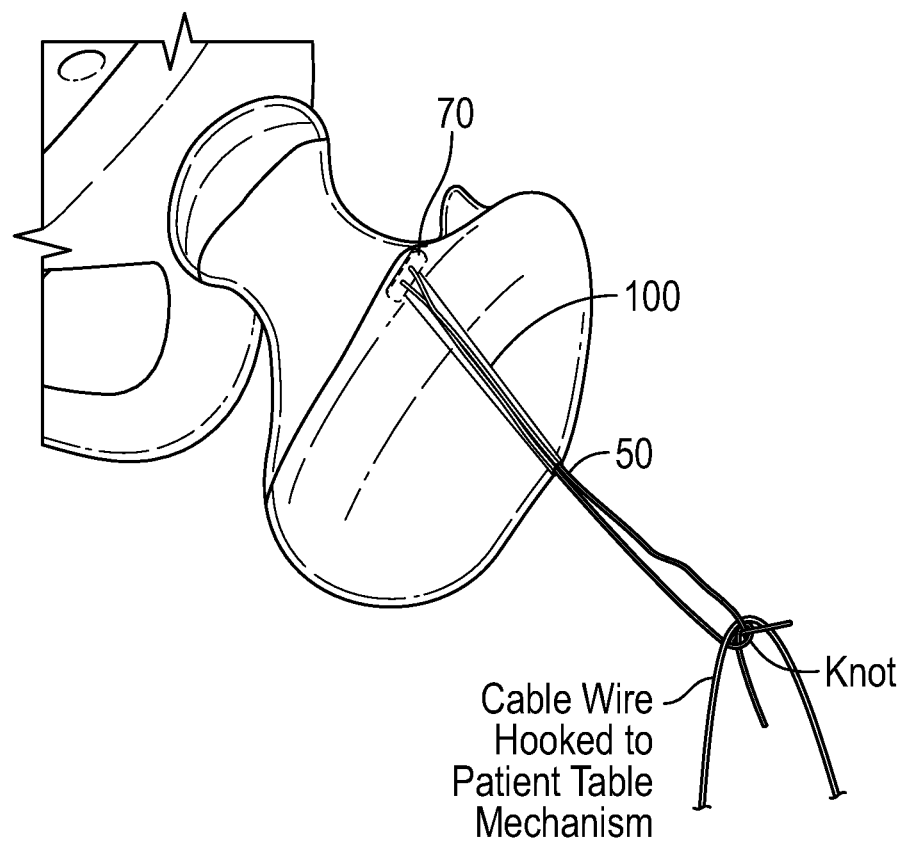
FIG. 1 is a perspective view of a suture button anchor assembly, deployed in a transosseous tunnel.

There is a need for an internal joint distracter and procedures which act to open and close the joint with lower force loads while avoiding peripheral nerve and tissue damage. Disclosed herein are medical devices and methods for internally distracting joints by using minimally invasive distraction. Distraction devices (anchor assembly) as disclosed herein can be used in medical procedures for treating, correcting, and/or repairing damage/diseased articular joints, e.g., avascular necrosis of the hip, arthritis in younger people, femoral-acetabular impingements (a condition where the hip bones have an abnormal shape), or Chondrolysis (gradual degradation of hyaline cartilage in the hip joint), worn or diseased aspects of the bones forming the joint.

In a disclosed embodiment, a distraction device is installed within or against a bone of a bone joint and force is applied to the device/anchor assembly to distract the joint bones and separate and space articular surfaces from a joint socket.

In a disclosed embodiment, an anchor assembly is secured temporarily within or against a bone of a bone joint and force is applied to the anchor assembly to distract the joint bones and separate and space articular surfaces from a joint socket.

In an embodiment, a tunnel is formed and can extend completely through a portion of one bone, and a distraction device is installed in the tunnel.

In still a further disclosed embodiment, applying a pulling force to a distraction device distracts joint bones.

In a disclosed embodiment for distracting a bone joint, a passage is formed in one bone of a bone joint, an anchor assembly is arranged within the passage, and a force is directly applied to a component of the anchor assembly to separate and distract the bones of the bone joint.

In another disclosed embodiment for distracting a bone joint, a tunnel passage is formed in one bone of a bone joint, an anchor assembly is arranged in/within the tunnel passage, and a force is directly applied to a suture component of the anchor assembly to separate and distract the bones of the bone joint.

In a further disclosed embodiment for distracting a bone joint, a bone socket is formed in one bone of a bone joint, an anchor assembly is arranged in the socket, and a force is directly applied to a suture component of the anchor assembly to separate and distract the bones of the bone joint.

In a still further disclosed embodiment, an anchor assembly for joint distraction is installed in the distal epiphysis of a bone.

In other disclosed anchor embodiments, a suture-anchor construct is deployed in the transosseous tunnel/socket, and the suture is externally tensioned to distract the joint. The sutures can be attached to a tensioner on a treatment surgical/patient/table or bed which directly applies tension to the suture.

In another disclosed embodiment, the tensioner is a force application system that is capable of five degrees of motion, permit positional adjustable along the x-, y- and z-axes, and angularly and radially.

In a further disclosed anchor embodiment, a suture anchor is provided, e.g., the anchor is externally threaded and inserted into the lateral aspect of the greater trochanter. The sutures are then attached to a treatment table or bed with an external tensioning device which directly applies tension to the suture.

In one disclosed embodiment, a distraction procedure involves inserting and passing an anchor/button construct which includes a suture/cable through a hole in joint bone and applying force to the suture/cable by a force application device, such as a spool or reel, to directly apply a distracting force to the bone.

In another disclosed embodiment, a distraction procedure includes an anchor or button construct with heavy gauge suture or cable, which is passed through a prepared tunnel and affixed to the bone. The suture/cable can be percutaneously removed and attached to a force application system, such as a spool or reel statically mounted to a rail adapter of a surgical/patient table. A handle/crank or other suitable system can be used to rotate the spool or reel in a clockwise or counter clockwise direction to increase or decrease the amount of force applied to the suture/cable. Instead of a user controlled system an automated system can be provided.

In a still further disclosed embodiment of a distraction procedure, a tunnel is prepared in a joint bone, an anchor or button construct with heavy gauge suture or cable is passed through the prepared tunnel, the anchor/button is affixed to the bone, and suture or cable is percutaneously removed and attached to a force/tension application device (force applicator), such as a spool or reel statically mounted on a surgical table, such as a Clark rail adapter/clamp, associated with a patient table.

In a still further disclosed embodiment, a sheath is inserted into a joint through the greater trochanter via a drilled pilot hole. Then a blunt tipped screw is inserted through that sheath until it reaches the anterior inferior iliac spine on the acetabulum. The screw is twisted in a clockwise direction, and the femoral head is distracted away from the acetabulum. The medical procedure is completed in the joint and the screw and sheath are removed.

Another disclosed embodiment is a distraction kit that includes at least one of a first distraction device, a second distraction device and a third distraction device, wherein the first, second and third distraction devices are the same or different, and one distraction device includes a cannulated anchor and force applicator, and the second and third distraction devices include suture anchor constructs.

These and other embodiments of the invention will become apparent from the following detailed description when read in conjunction with the accompanying drawings and illustrated exemplary embodiments of the invention.

In the following detailed description, reference is made to various embodiments. It is to be understood that other embodiments may be employed, and that structural and logical changes may be made without departing from the scope of the disclosure herein.

Figure 2:
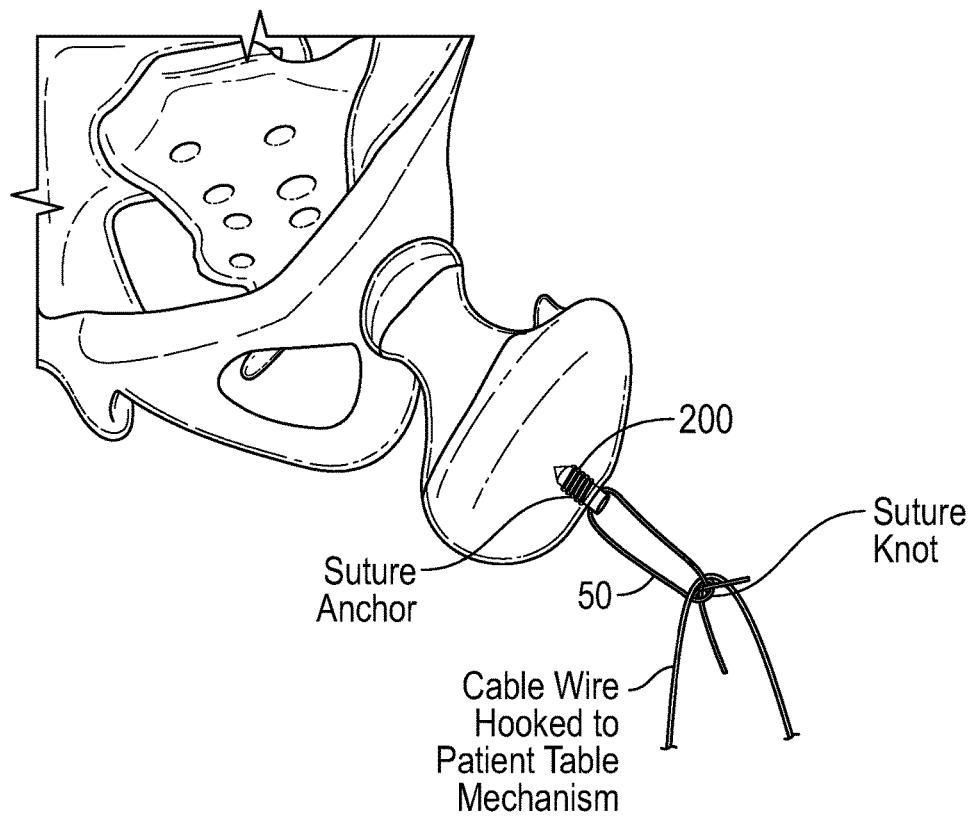
FIG. 2 is a perspective view of a suture-anchor anchor assembly, deployed in ta transosseous socket.
Figure 3:
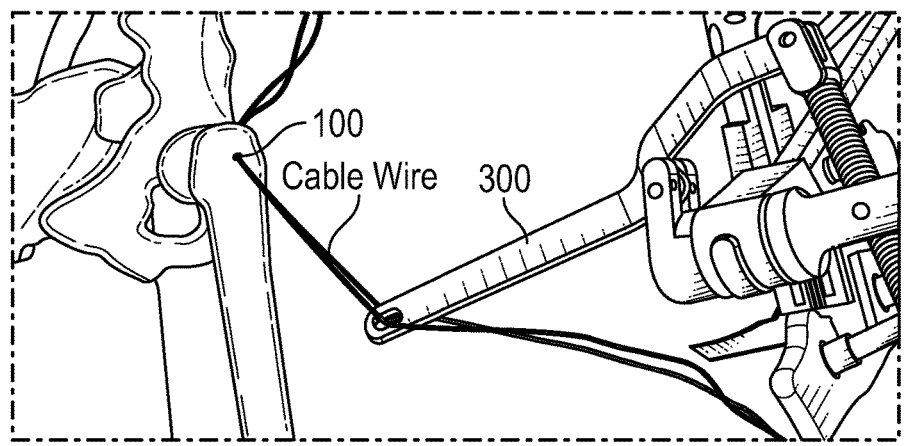
FIG. 3 is a perspective view of anchor assembly suture attached to a force application device of a patient table.

In FIGS. 1 and 2 joint distraction utilizing less force and causing less collateral damage than existing joint distraction systems is accomplished by using anchor assemblies that include a suture 50, e.g., the sutures can be affixed to the bone in any suitable fashion, for example with a button 70 having a first minor dimension sufficient to pass through the tunnel and a second major dimension sufficient to span the tunnel diameter, e.g., BicepsButton™ (FIG.1), to engage a distal side of the bone so that the joint can be distracted when the suture is pulled. A small transosseous tunnel 100 to pass a suture and suture button combination (FIGS. 1 and 3), or socket 200 for an anchor (FIG. 2) (e.g., a Corkscrew® anchor) is prepared. Suitable drill guides that confer the surgeon the ability to target bones from outside the joint, involving an alignment bar, such as that disclosed in U.S. Patent Publication No. 2014/0276841 or an articulating drill guide, such as that disclosed in U.S. Patent Publication No. 2014/0114322, may be used. The sutures exit percutaneously and are attached to a distraction device, as shown in FIGS. 3-6. The distraction device (e.g., cable/suture end of the BicepsButton™ or Corkscrew® anchor) is attached to a bed rail component 300 of a patient table (FIG. 3), or hook 690 and is pulled by a spool or reel mechanism, such as a Clark rail reel mechanism that can be adjusted up/down and/or side by side to achieve ideal distraction angle.

Figure 4:
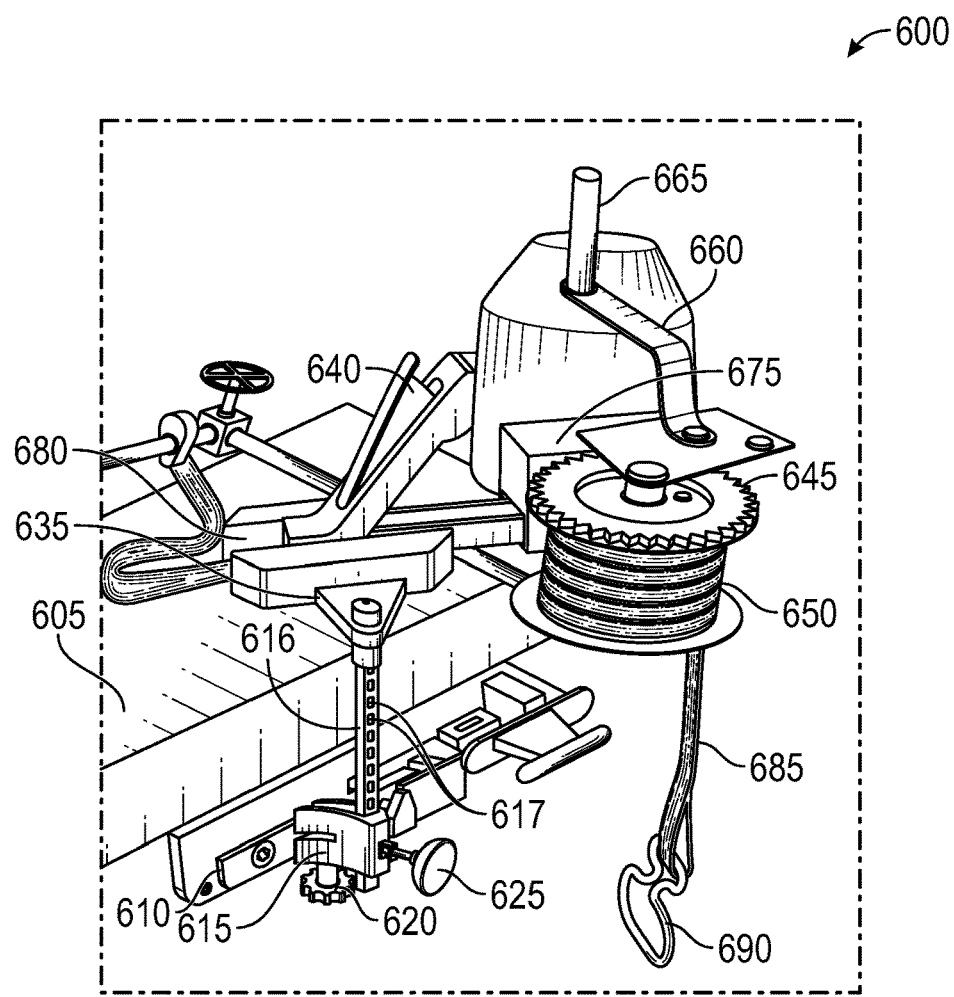
FIG. 4 is a side perspective view of the force applicator system for a patient/surgical table that allows the pulling/tensioning vector to be changed.
Figure 5:
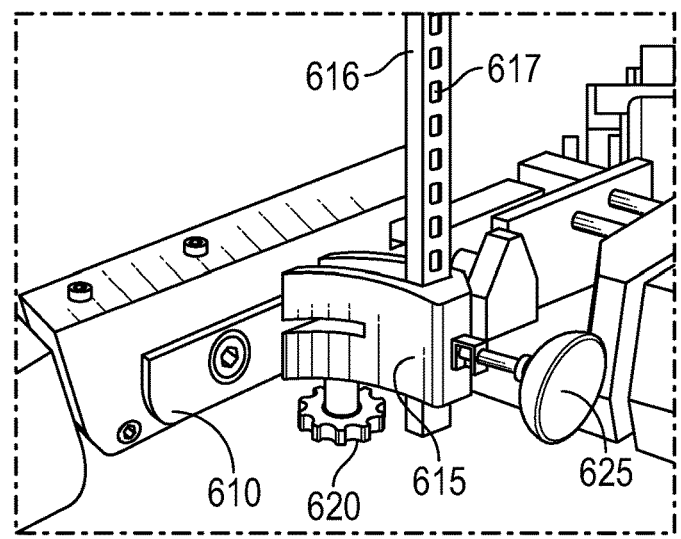
FIG. 5 is a perspective view of an adapter to attaching a force application system to surgical/patient table rail.
Figure 6:
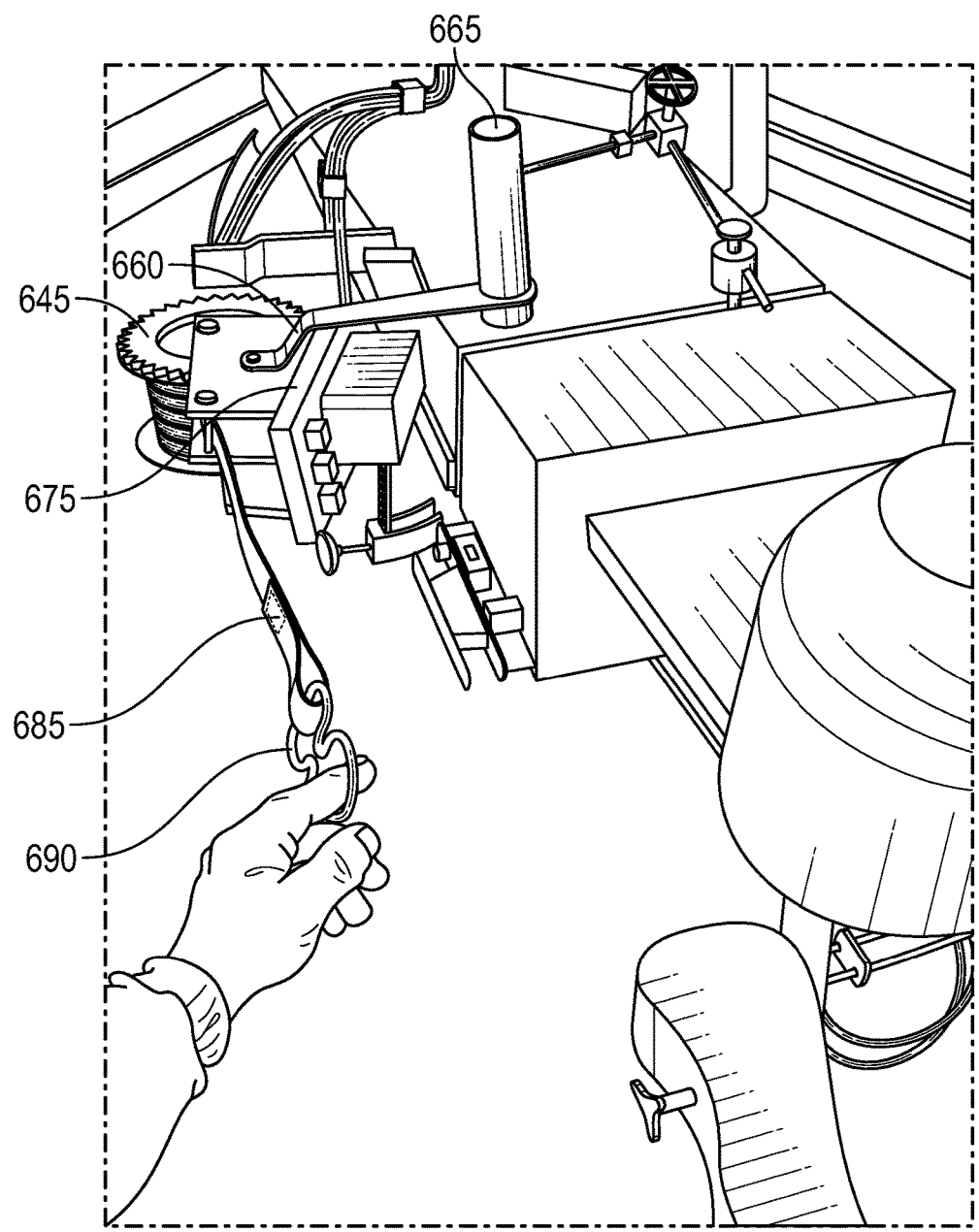
FIG. 6 is a front perspective view of the surgical/patient table and force application system with a suture from implant loaded onto the hook of the reel/spool device of the force application system.

FIGS. 4-6 illustrate the force applicator system associated with a surgical/patient table. In FIG. 4, force applicator system 600 is secured to a patient table 605 by rail adapter/clamp 615 which can slide onto and along the Clark rail 610. The system also includes a reel/spool housing 645, a housing mounting frame 675, and a platform 635 upon which the frame 675 is located. The frame 675 supports the reel/spool housing 645 for rotation, and the platform supports the frame 675 for both reciprocal and angular repositioning to adjust the force vector for the reel/spool wire/cable. The frame 675 includes a handle 640 which reciprocally slides within a channel on the platform of the frame.

The adapter/clamp 615 includes a vertical hole through which post 616 extends. Post 616 is provided with a plurality of equally-spaced holes or openings 617 that allow more manual adjusting of the height of the device (relative to the rail 610, for example) by the pulling knob 625 that include a shaft (not shown) that can be moved into and out of the openings 617. Knob 625, e.g., a height adjustment knob can be of any geometry, round, oval, scalloped, to allow the vertical position of the surgical leg positioning device 100 to be adjusted as needed.

FIG. 5 shows the close-up view of the adapter/clamp 615, which also includes knob 620, which allows the rail adapter/clamp and post 610 to move axially along the rail 610. This adjustment can be effected prior to tightening the adapter/clamp 615 by the manual tightening of knob 620 which locks the post and supported components in a desired position. Knob 620 may have a scalloped configuration, for ease of manipulation. Knob 16 allows the rail adapter/clamp 20 to slide along the operating room bed rail 21 until in the desired position and then tightened to secure the rail adapter/clamp 20 in position for securing and unsecuring the rail adapter/clamp from the rail 610 for movement along the surgical/patient table.

The platform 635 is located at the top of post 616. The vertical position of the platform can be adjusted by pulling on knob 625. Knob 625 includes a cylindrical shaft (not shown) that is positionable within any one of the plurality of holes 617 in post 616 by pulling/withdrawing the knob and moving the platform in the vertical direction.

Platform 635 includes upper and lower sections that can rotate relative to one another, and includes a base plate (lower plate or section) that is connected to a rotational positioning plate (upper plate or section) by a swivel lock (not shown) which when loosened by manual/automatic operation, allows the rotational positioning base to articulate with respect to the base plate and to pivot or rotate the frame 675 and housing 645. Post 615, described above, are rigidly connected to base/lower plate/section which positions and supports in cantilever fashion rotational positioning upper/base. The rotational base plate, e.g., upper plate, includes open channel 680 for locating therein an arm of the frame 675. A locking handle 640 extends from a proximal end of the frame arm and permits repositioning movement along the channel. Platform 635 provide for both reciprocating and angular repositioning of the reel/spool housing.

Reel 645 of cable 650 is rotatably mounted on platform 635, and can be rotated or turned via handle 665 which extends from the crank 660. Any other suitable device, instead of the mechanical-user controlled reel rotation can be used, such as an automated system. In FIG. 6, the reel is mounted for rotation within a frame 675. Wire on the reel is attached to a proximal end of a tether/strap 685. A hook 690 is arranged at the distal end of the tether/strap 685.

The suture from anyone of the above embodiments can be connected to the hook 690 and the handle-crank rotated to increase tension on the sutures thereby pulling the femoral head out of the hip joint. Rotating the reel/spool in the opposite direction releases tension on the sutures so that the femoral head can return to is natural positon within the hip joint.

Although the present disclosure has been described in connection with preferred embodiments, many modifications and variations will become apparent to those skilled in the art. It should be understood that the above disclosure and embodiments therein are exemplary and are not to be considered as limiting.

What is claimed is:

1. A method of distracting a bone joint, comprising: forming a passage in one bone of a bone joint; inserting an anchor assembly into the passage; temporarily securing the anchor assembly to the one bone; and applying a force directly to the anchor assembly to separate and distract the one bone from another bone of the bone joint, wherein the passage is a tunnel that extends completely through a portion of the one bone, wherein inserting the anchor assembly in the passage comprises passing an anchor of the anchor assembly completely through the tunnel, and passing the anchor comprises passing a button through the tunnel to engage the bone wall and temporarily secure the anchor.

2. The method of claim 1, wherein the bone joint is between a femoral head and an acetabulum.

3. The method of claim 1, wherein the arranging an anchor assembly in the passage comprises positioning an anchor of the anchor assembly within the tunnel.

4. The method of claim 3, wherein the anchor assembly comprises a suture attached to the anchor, and the suture is percutaneously removed and the force is applied to the suture.

5. The method of claim 1, wherein the anchor assembly comprises a suture, and the suture is percutaneously removed and the force is applied to the suture.

6. The method of claim 1, wherein a distraction device is attached to a bed rail component.

* * * * *